United States Patent [19]

Kado et al.

[11] Patent Number: 4,605,627
[45] Date of Patent: Aug. 12, 1986

[54] **PLASMID VEHICLE FOR CLONING IN *AGROBACTERIUM TUMEFACIENS***

[75] Inventors: Clarence Kado; Robert C. Tait; Ronald C. Lundquist, all of Davis, Calif.

[73] Assignee: The Regents of the University of California, Berkeley, Calif.

[21] Appl. No.: 501,959

[22] Filed: Jun. 7, 1983

[51] Int. Cl.[4] .................. C12N 1/00; C12N 15/00; C07H 15/12
[52] U.S. Cl. .................. 435/317; 536/27; 435/172.3; 935/29; 935/67; 935/6
[58] Field of Search ............... 435/317, 172.3; 536/27; 935/29

[56] References Cited

PUBLICATIONS

Tuite et al., The EMBO Journal vol. 1, No. 5, pp. 603-608, 1982.
Kado et al., Journal of Bacteriology, vol. 145, No. 3, pp. 1365-1373, Mar. 1981.
Hicks et al., Genetic Engineering, Principles and Methods, vol. 4, Plenum Press ed. by Sellov et al., pp. 219-226, (1982).
Chilton et al., Stadler Symp. vol. 13, pp. 39-52, Univ. of Missouri (1981).
Leemans et al., Molecular Biology of Plant Tumors, ed. by Kahl et al., pp. 537-573 (1982).
Depicke et al., J Mol and Applied Genetics, vol. 1, No. 6, pp. 561-573 (1982).
Ameres et al., Recombinant DNA, Proceedings of the Third Cleveland Symposium on Macromolecules, pp. 185-197, Jun. 22-26, 1981.

*Primary Examiner*—Alvin E. Tanenholtz
*Attorney, Agent, or Firm*—Bertram I. Rowland

[57] ABSTRACT

A cloning vector comprises a replication system derived from the pTAR plasmid and capable of stable maintenance in *Agrobacterium tumefaciens*. By combining the pTAR replication system with a second replication system from a host other than *A. tumefaciens*, shuttle vectors are obtained which allow manipulation in more than one host. The cloning vectors will usually include selectable markers having restriction enzyme sites which allow identification of recombinant molecules by insertional inactivation. By providing at least a fragment of the T-DNA region from the Ti plasmid, the subject vectors can be used to clone desired DNA fragments and transfer these fragments to the genome of a higher plant.

The strain *E. coli* HB101/puc0400 was deposited on June 7, 1983 at the A.T.C.C. for patent purposes and granted accession no. 39377.

8 Claims, 2 Drawing Figures

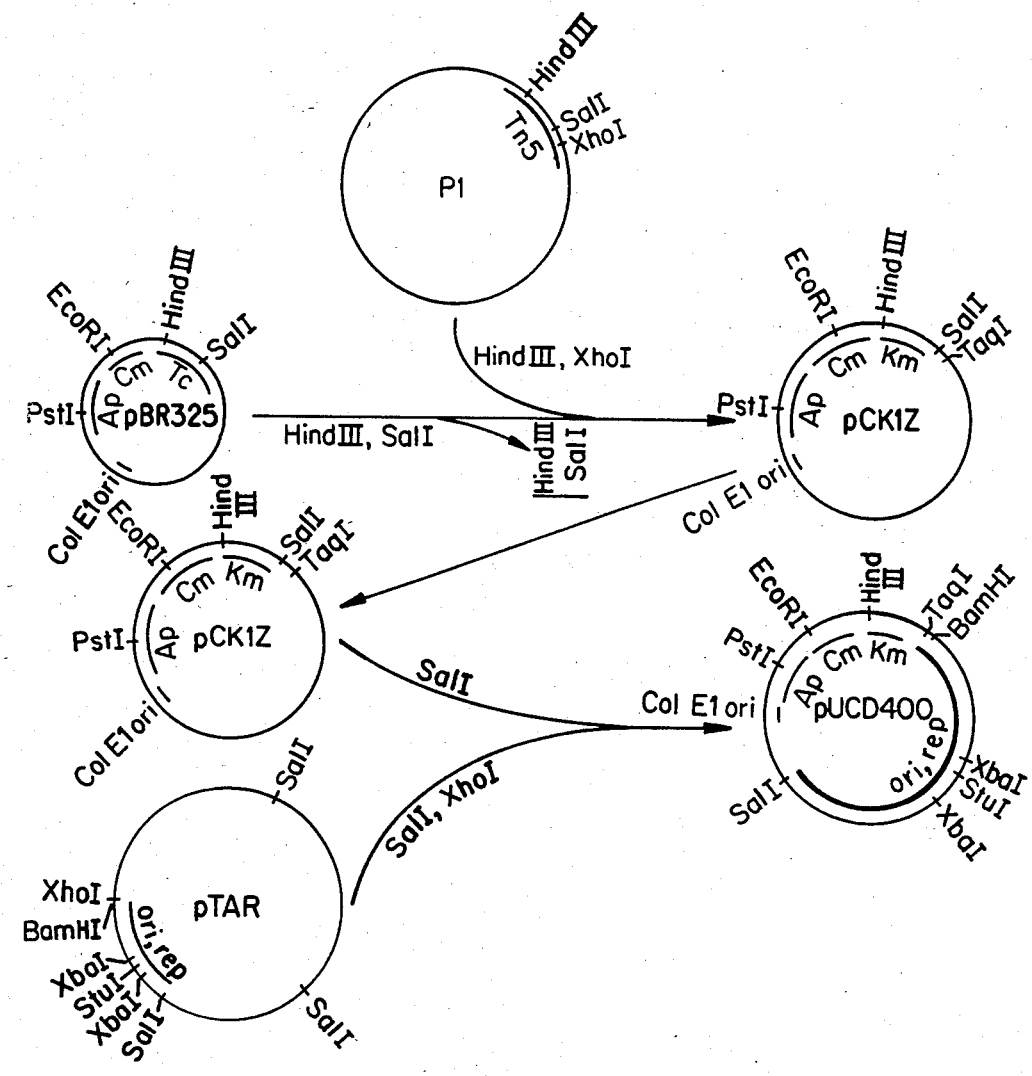
FIG._1.

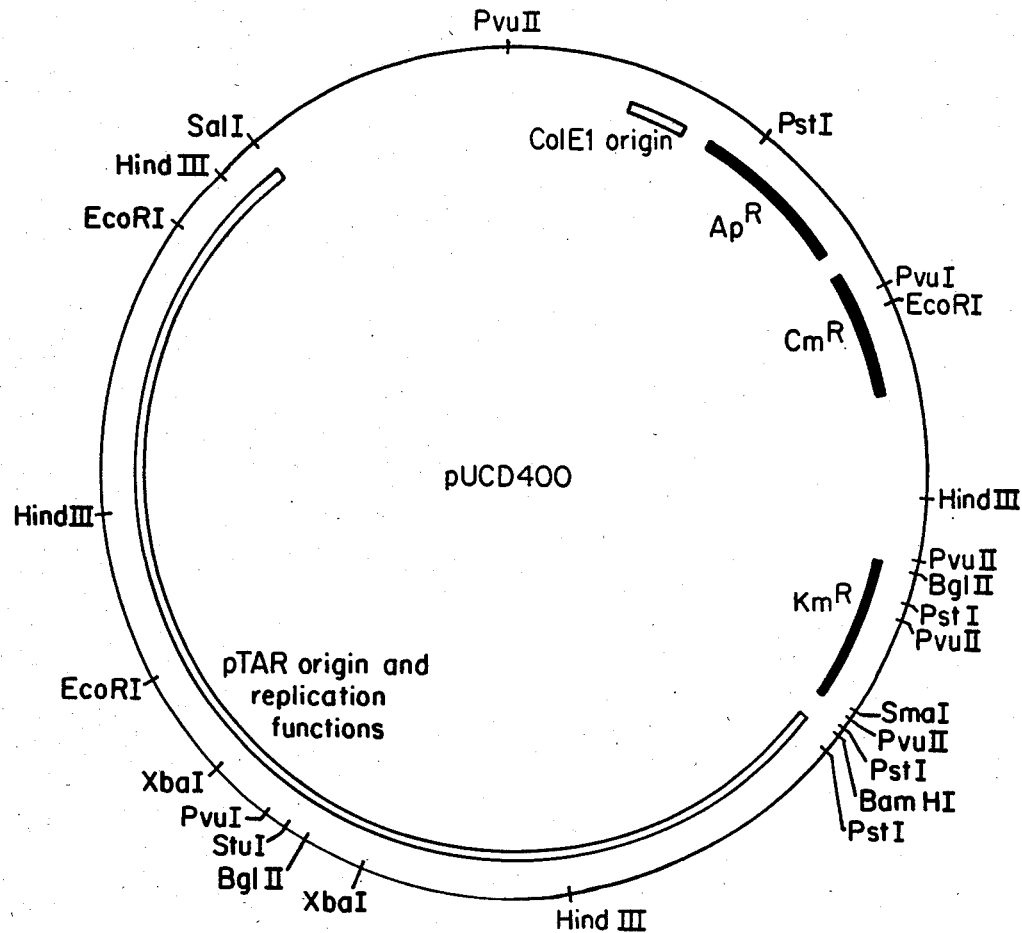
FIG.—2.

PLASMID VEHICLE FOR CLONING IN *AGROBACTERIUM TUMEFACIENS*

BACKGROUND OF THE INVENTION

1. Field of the Invention

Genetic manipulation of plant cells is an area of widespread interest. The ability to confer desirable traits, such as disease resistance, environmental resistance, enhanced yield, and the like, is of great economic and scientific importance. In order to genetically manipulate plant cells, it is necessary to develop systems for the delivery and integration of desired structural genes into the plant genome.

Heretofore, research has centered on the use of DNA plant viruses and the Ti plasmid of *Agrobacterium tumefaciens* for use as vectors to introduce DNA into higher plants. Both of these proposed systems suffer from inherent limitations. DNA plant viruses, such as the cauliflower mosaic virus (CaMV), have restricted host ranges and often lose infectivity after manipulation. Moreover, recombinant CaMV molecules might be too big to be packaged into virus particles, limiting their usefulness. Also, there is no evidence that CaMV DNA integrates into host cell chromosomes. Without integration, it is unlikely that the recombinant molecule would be transmitted to progeny of the infected plant.

In contrast, incorporation of Ti plasmid DNA into plant cells has been reported. Hernalstens et al. (1980) Nature 287:654-656, and Garfinkel et al. (1981) Cell 27:143-153. More importantly, it has been found that foreign DNA inserted into the Ti plasmid in the region near the T-DNA can be incorporated into the plant genome. Despite these promising results, use of the Ti plasmid as a vehicle for introducing DNA into higher plants remains problematic. The Ti plasmid can be maintained only in *A. tumefaciens* which is not a convenient host for in vitro manipulation. Also, the Ti plasmid is very large (usually above 200 kbp) further rendering manipulation difficult, particularly when relatively large DNA fragments have been inserted. Finally, maintenance of the Ti plasmid in *A. tumefaciens* is less stable than would be desired.

For these reasons, it would be desirable to provide a cloning vehicle which could be stably maintained in other more convenient hosts, such as *E. coli*; as well as *A. tumefaciens*. Such vectors would allow insertion and manipulation of foreign DNA in the *E. coli* followed by introduction into *A. tumefaciens*. It is further desirable that the vectors include a plurality of selectable markers and be sufficiently small in size to accommodate relatively large DNA inserts. Finally, it would be desirable that the vector be able to transfer the inserted foreign DNA into the genome of a higher plant.

2. Description of the Prior Art

The pTAR plasmid was described by Kado et al. (1981) J. Bacteriol. 145:1365-1373. Plasmid pUCD400 (formerly pCK2D) was first described in Kado et al. (1982) Proc. Fourth Intl. Symp. Genetics Indust. Microorg., Kyoto, Japan.

SUMMARY OF THE INVENTION

Novel DNA segments useful for constructing plasmid cloning vehicles capable of stable maintenance in *Agrobacterium tumefaciens* are provided. Plasmid cloning vehicles of the present invention are characterized by an origin of replication and associated replication functions derived from the pTAR plasmid and at least one restriction site in a non-essential region capable of receiving exogenous DNA fragments. Conveniently, the cloning vehicle will be a shuttle vector including a second replication system capable of stable maintenance host(s) other than *A. tumefaciens* and will have one or more selectable markers, as well as restriction sites located in at least some of the selectable markers. The second origin of replication allows the vector to be manipulated in more convenient hosts, such as *E. coli*, while the selectable markers allow for easy identification of recombinant plasmids. It has been found that plasmids constructed from cloning vehicles having the pTAR replication system are very stably maintained in *A. tumefaciens*.

BRIEF DESCRIPTION OF THE DRAWINGS

FIG. 1 illustrates the construction of the pUCD400 plasmid from pBR325 and bacteriophage P1.

FIG. 2 is a restriction map of the pUCD400 plasmid.

DESCRIPTION OF THE SPECIFIC EMBODIMENTS

Methods and compositions are provided for the introduction of exogenous DNA in *Agrobacterium tumefaciens* and for integration of said exogenous DNA into the genome of a higher plant. Plasmid vehicles which comprise an origin of replication and associated replication functions substantially identical to those of the pTAR plasmid are employed. Desirably, such plasmid vehicles will be shuttle vectors including a second origin of replication capable of stable maintenance in host(s) other than *A. tumefaciens* and will have at least one marker for selection and at least one restriction site in a region non-essential to the stable maintenance of the plasmid.

The plasmid vehicle of the present invention should be relatively small, allowing insertion of relatively large fragments of exogenous DNA without substantially reducing the viability of the recombinant plasmid. Usually, the plasmid will be less than 50 kbp (kilobase pairs) in length, more usually below about 40 kbp. For the most part, the plasmid vehicles will be from 10 to 25 kbp, more often from 15 to 25 kbp.

The origin of replication and associated replication functions of the pTAR plasmid are located within a 7.5 kbp region flanked by XhoI and SalI restriction sites, as illustrated in FIG. 1. This region may be excised from the pTAR plasmid using the specified restriction endonucleases and purified according to well known techniques to provide a source for the replication system of the present invention. The 7.5 kbp fragment can be used without modification or be chewed back using exonucleases to reduce its length to the minimum compatible with continued replication. In this way, the overall size of the constructed cloning vehicle can be reduced. The isolated DNA fragment carrying the pTAR origin can then be combined with other functions, either directly or using linkers as necessary, to provide a plasmid cloning vehicle having a set of desired characteristics.

The second replication system may be eukaryotic or prokaryotic, usually being prokaryotic, more usually being capable of replication in *E. coli* to provide for convenient manipulation and amplification. Suitable replication systems for *E. coli* are well known and may be derived from plasmids such as pBR322, pBR325, and bacteriphages. Replication systems for other Gram-negative bacteria include RSF1010, and pRK290, while plasmids such as pBD6 and pSL103 carry replication systems suitable for the Gram-positive bacteria *Bacillus subtilis*. Eukaryotic replication systems may be derived from the 2 μm plasmid or from autonomously replicating sequences as first described by Struhl et al. (1979) Proc. Nat. Acad. Sci. USA 76:1035–1039.

While not always essential, particularly where the exogenous DNA provides a means for selection, it will normally be desirable to provide a marker as part of the cloning vehicle to allow for selection of transformants. A wide and diverse variety of markers may be employed. Conveniently, antibiotic resistance may be employed which allows for selection of transformants by culturing the cells on a medium containing the particular antibiotic. Antibiotic resistance can be provided to ampicillin, penicillin, tetracycline, kanamycin, etc. Resistance can also be provided to heavy metals. Alternatively, prototrophy can be provided to an auxotrophic host. That is, a host lacking the ability to produce an essential metabolite is transformed with the vehicle which provides the structural genes necessary for the enzymes for producing the metabolite. By culturing the transformants in a culture medium lacking the essential metabolite, the transformants can be selected. Other more sophisticated techniques include providing incompatibility to particular bacteriophage strains, resistance to toxins, changes in morphology, and the like. In some instances, it will be desirable to have a plurality of markers, where one of the markers has a restriction site for insertion of the exogenous DNA. The loss of the property provided by the marker allows for detection of plasmids into which the exogenous DNA has been inserted. Other alternatives exist for monitoring for plasmids having the desired exogenous DNA. When constructing a plasmid vehicle capable of replication in host in addition to *A. tumefaciens*, it will often be useful to provide marker(s) capable of expression in such additional hosts as well as *A. tumefaciens*.

The cloning vehicle will normally have at least one unique restriction site for a restriction enzyme and may have a number of unique restriction sites for the equivalent number of restriction enzymes. The restriction sites will be in non-essential areas of the cloning vehicle, so as not to disturb the functioning of the plasmids. Conveniently, at least some of the restriction sites will be present in the gene(s) responsible for the selectable markers. In that way, recombinant plasmids having insertions in such restriction sites may be further selected by loss of the phenotype associated with the marker.

Plasmid cloning vehicles constructed according to the present invention are very stable, being resistant to curing by heat and chemicals such as ethidium bromide, acridine orange, mitomycin C, and the like. Moreover, the plasmids exist in multiple copies and can be amplified by treatment with spectromycin.

The construction of a particular plasmid (pUCD400) in accordance with the present invention is illustrated in FIG. 1 and described in the Experimental section hereinafter. A more detailed restriction map of the pUCD400 plasmid is set forth in FIG. 2. The plasmid contains origins of replication from pTAR and ColE1 (derived from pBR322) and can be introduced into either *E. coli* or *A. tumefaciens* by transformation. Transformants can be selected based on kanamycin resistance (Km$^r$), ampicillin resistance (Ap$^r$), and chloramphenicol resistance (Cm$^r$). Recombinant plasmids can be detected by the loss of anitbiotic resistance resulting from insertion into one of the resistance genes, e.g. at the PstI site in the Ap$^r$ gene, the SmaI site in the Km$^r$ gene, or the EcoRI site in the Cm$^r$ gene. Additionally, the StuI, BglII and XbaI sites are in non-essential regions of the plasmid and available as cloning sites.

The plasmid vehicles of the present invention are useful as cloning vehicles in *A. tumefaciens*. In particular, by isolating the replication system (including both the origin of replication and associated replication functions) of the pTAR plasmid and combining said replication system with other DNA sequences having certain desired functions, superior cloning vehicles can be constructed. The incorporation of a second origin of replication provides a shuttle vector capable of stable maintenance in both *A. tumefaciens* and other hosts, such as *E. coli*. Moreover, inclusion of selectable marker(s) facilitates identification of transformants, and the availability of the restriction sites within at least some of said markers allows identification of recombinant molecules based on insertional inactivation of the marker.

In addition to the usefulness as a cloning vehicle in *A. tumefaciens*, the vectors of the present invention can be employed to transfer foreign genes into higher plants. A fragment of the T-DNA from a Ti plasmid is introduced into the subject vector. A foreign gene is then introduced into the T-DNA. Conveniently, these manipulations can be carried out in a well-characterized host, such as *E. coli*. After a plasmid has been constructed having the desired gene within the T-DNA region, the plasmid can be transformed into a *A. tumefaciens* strain carrying the infective Ti plasmid. The foreign gene present in the T-DNA of the subject vector can then transfer to the Ti plasmid by homologous recombination. The gene can then be transferred to the genome of higher plants through the normal infection process of *A. tumefaciens*.

The following experiments are offered by way of example and not by way of limitation.

EXPERIMENTAL

Materials and Methods

Restriction enzymes were either purchased from New England Biolabs (Beverly, MA) or Bethesda Research Laboratories, Inc. (Rockville, MD), or were purified. Phage P1::Tn5 was obtained from Dale Kaiser. Plasmid DNA from *E. coli* was isolated and purified as described by Tait et al. (1982) Mol. Gen. Genet. 186:10–15. Plasmid DNA from *Agrobacterium tumefaciens* was isolated and purified according to Farrand et al. (1981) Mol. Gen. Genet. 181:44–51. Cleavage and ligation with restriction endonucleases and T4 ligase were carried out as recommended by the supplier (New England Biolabs). Plasmids and plasmid fragments were analyzed by the rapid mini-screen procedures described previously by Bolivar (1978) "Genetic Engineering" (ed. Boyer and Nicosia) Elsevier/North Holland Biomedical Press, pp 59–63. Crown gall tumor and virulence assays were performed on sunflower according to Loper et al. (1979) J. Bacteriol. 139:591–596.

Construction of pUCD400 pUCD400 was constructed from phage P1 and plasmid pBR325, as illustrated in FIG. 1. The structural gene for kanamycin (neomycin) phosphotransferase II (KPT) was cleaved from Tn5 (carried in phage P1) with restriction enzymes HindIII and XhoI, leaving behind the insertion sequences that originally flanked the gene.

The KPT gene was inserted into a slot formed by removing the HindIII-SalI fragment from the tetracycline resistance (Tc$^r$) region of pBR325. The resulting recombinant plasmid (pCK1Z) thus carried the KPT gene in the position of the Tc$^r$ gene. pCK1Z may be used as a conventional vector in *E. coli* and possesses a single BglII site in the KPT gene into which fragments generated by BglII could be inserted.

The replication region of pTAR was excised by digestion with SalI and XhoI and the resulting fragment was inserted into the SalI site of pCK1Z. The resulting hybrid plasmid was designated pUCD400 and replicated efficiently in *A. tumefaciens* and *E. coli*, and was amplifiable in *E. coli* with spectinomycin (Sp). pUCD400 contains unique sites for the following restriction enzymes: BamHI, StuI, SmaI, and SalI. In addition, the small (1 kb) XbaI fragment in pUCD400 can be deleted leaving a single XbaI site for cloning XbaI generated fragments.

In accordance with the subject invention, a novel vector allows cloning in *A. tumefaciens* as well as other hosts. *The vector provides restriction enzyme sites not found on other A. tumefaciens cloning vehicles.* Moreover, plasmids constructed using the subject vectors are found to be particularly stable when compared to other plasmids capable of transforming *A. tumefaciens*.

Although the foregoing invention has been described in some detail by way of illustration and example for purposes of clarity and understanding, it will be obvious that certain changes and modifications may be practiced within the scope of the appended claims.

What is claimed is:

1. A DNA fragment of less than 10 kbp which includes a sequence that corresponds identically with that which possesses the minimum compatible with continued replication and which is derived from the origin of replication and associated replication functions which are located on a 7.5 kbp XhoI/SalI restriction fragment of the pTAR plasmid.

2. A DNA sequence as in claim 1, which sequence is obtained by cloning the 7.5 Kbp fragment of the pTAR plasmid flanked by XhoI and SalI restriction endonuclease sites.

3. A shuttle vector including a DNA fragment according to claim 1, and a second origin of replication which provides stable maintenance in hosts other than *A. tumefaciens*.

4. A shuttle vector as in claim 3, wherein the second origin or replication provides stable maintenance in other Gram-negative bacteria.

5. A shuttle vector as in claim 4, wherein the second origin provides stable maintenance in *E. coli*.

6. A shuttle vector as in claim 3, further including at least a portion of the T-DNA region derived from a Ti plasmid.

7. A shuttle vector as in claim 6, having a structural gene foreign to the pTAR plasmid inserted sufficiently close to the T-DNA so that said structural gene can be transferred to a Ti plasmid by homologous recombination.

8. pUCD400.

* * * * *